United States Patent
Schloss et al.

(10) Patent No.: US 7,010,346 B1
(45) Date of Patent: Mar. 7, 2006

(54) IMPLANTABLE MEDICAL DEVICE HAVING ATRIAL TACHYARRHYTHMIA PREVENTION THERAPY

(75) Inventors: Harold C. Schloss, Los Angeles, CA (US); Mark W. Kroll, Simi Valley, CA (US); Paul A. Levine, Santa Clarita, CA (US)

(73) Assignee: Packsetter, Inc., Sylmar, CA (US)

( * ) Notice: Subject to any disclaimer, the term of this patent is extended or adjusted under 35 U.S.C. 154(b) by 775 days.

(21) Appl. No.: 09/931,481

(22) Filed: Aug. 15, 2001

Related U.S. Application Data

(63) Continuation of application No. 09/338,216, filed on Jun. 22, 1999, now Pat. No. 6,292,694.

(51) Int. Cl.
*A61N 1/18* (2006.01)

(52) U.S. Cl. .................................................. 607/14

(58) Field of Classification Search .............. 607/14, 607/9; 600/509
See application file for complete search history.

(56) References Cited

U.S. PATENT DOCUMENTS

| | | | |
|---|---|---|---|
| 5,042,497 A | 8/1991 | Shapland | 128/696 |
| 5,514,161 A | 5/1996 | Limousin | 607/9 |
| 5,674,251 A | 10/1997 | Combs et al. | 607/4 |
| 5,902,324 A * | 5/1999 | Thompson et al. | 607/9 |
| 6,058,328 A * | 5/2000 | Levine et al. | 607/14 |

* cited by examiner

Primary Examiner—Mark Bockelman

(57) ABSTRACT

An implantable medical device provides atrial arrhythmia prevention pacing when an interatrial conduction disturbance is detected. The implantable medical device includes a signal processor that detects the interatrial conduction disturbance and a pulse generator circuit coupled to the detector that delivers the atrial arrhythmia prevention pacing pulses to the heart when the processor detects the interatrial conduction disturbance. The interatrial conduction disturbance may be a P-wave duration, a difference between odd and even P-waves, or a predetermined P-wave spectral energy distribution.

12 Claims, 3 Drawing Sheets

IMPLANTABLE MEDICAL DEVICE HAVING ATRIAL TACHYARRHYTHMIA PREVENTION THERAPY

This application is a continuation of Ser. No. 09/338,216, filed Jun. 22, 1999, now U.S. Pat. No. 6,292,694.

FIELD OF THE INVENTION

The present invention is generally directed to an implantable medical device. The present invention is more particularly directed to an implantable medical device which provides atrial fibrillation prevention pacing therapy to a heart upon detecting an interatrial conduction disturbance predictive of a pathological atrial tachyarrhythmia.

BACKGROUND OF THE INVENTION

Atrial fibrillation is a common cardiac arrhythmia. Although not life-threatening, it is associated with stroke and congestive heart failure. Further, patients with atrial fibrillation can experience palpitations of the heart and even dizziness. In short, atrial fibrillation can substantially reduce quality of life.

While drug therapy for atrial fibrillation is available, many patients either are, or become, refractory to such therapy. Drug therapy can also cause undesirable side effects.

Internal cardioversion of atrial fibrillation is also known. This therapy, however, is not widely or commercially available.

External cardioversion of atrial fibrillation is often the last resort for atrial fibrillation patients. However, this therapy generally requires a hospital stay and can be traumatic.

Atrial fibrillation is a progressive disease. In early stages it can be paroxysmal in nature. Many patients with sick sinus syndrome also experience or may develop paroxysmal atrial fibrillation. Research has been conducted to determine if there are predictors of paroxysmal atrial fibrillation. For example, Liu et al (PACE, Vol. 21:79–86) reported that prolongation of P-wave duration is an indicator of interatrial conduction disturbance. They also reported that prolongation of P-wave duration is an indication of sick sinus syndrome and that in those patients, the prolongation of P-wave is associated with an increased incidence of paroxysmal atrial fibrillation. Further, Jordaens et al (JCE 1998: 530–534) concluded that it is possible to recognize patients with paroxysmal atrial fibrillation using P-wave signal averaging. They also concluded, however, that its role in the clinical management of patients remained unclear.

Further, Montereggi et al (AJC 1996:266–269) evaluated the correlation between the signal-averaged P-wave duration and the occurrence of paroxysmal atrial fibrillation in hyperthyroid patients with and without a history of atrial fibrillation. They concluded that a P-wave duration cut-off value of 130 ms held specificity, sensitivity, and positive predictive accuracy values of 79%, 85%, and 83%, respectively.

Still further, Cecchi et al (Heart 1997: 44–99) assessed the relationships between P-wave duration and the occurrence of atrial fibrillation in hypertrophic cardiomyopathy. In assessing risk for atrial fibrillation, they reported that P-wave duration greater than 140 ms was associated with sensitivity, specificity, and positive predictive accuracy values of 56%, 83%, and 66%.

While P-wave duration has been found to indicate an interatrial conduction disturbance and provide a predictive tool with respect to paroxysmal atrial fibrillation, other work was also conducted. For example, Stafford et al. (BrHeartJ 1995: 413–418) used spectral analysis.

Spectral analysis was performed on the entire P-wave. The P-wave signals were filtered with a high pass of 15 Hz before Fourier transformation to attenuate large low frequency components. P-wave energy was estimated by summating the energies contained in frequency bands extending from 20, 30, 40, 60 and 80 to 150 Hz. Each was expressed as an absolute value and in an energy percentage ratio. They found that paroxysmal atrial fibrillation patients had more energy in the higher frequency bands of the P-wave and greater spatial velocity.

While the foregoing evidences new diagnostic tools for paroxysmal atrial fibrillation, the use of these tools in an implanted device to trigger atrial arrhythmia prevention therapy has not been addressed. More specifically, as these patients are generally already being treated with an implantable cardiac rhythm management device, it would be advantageous if such a device could also detect an interatrial conduction disturbance and provide atrial arrhythmia prevention therapy responsive thereto in addition to the traditional therapies for sick sinus syndrome. More particularly, it would be advantageous to have an implantable medical device capable of employing additional methods of identifying disease progress towards paroxysmal atrial fibrillation prior to its actual start and then applying pacing therapies to prevent the start of an atrial arrhythmia such as atrial fibrillation. The present invention provides such an implantable medical device.

SUMMARY OF THE INVENTION

The present invention provides an implantable medical device for detecting an interatrial conduction disturbance and provides atrial tachyarrhythmia prevention stimulation in response thereto. In a preferred embodiment, the present invention provides an implantable medical device including a sensing system that senses atrial activity of a heart and a discriminator, coupled to the sensing system, that determines if a selected characteristic of the detected atrial activity satisfies a predetermined criteria indicative of an interatrial conduction disturbance. The implantable medical device further includes a pulse generator circuit, coupled to the discriminator, that delivers atrial arrhythmia prevention pacing pulses to the heart responsive to the discriminator determining that the selected characteristic of the sensed atrial activity satisfies a predetermined criterion.

In accordance with one aspect of the present invention, the interatrial conduction disturbance is a P-wave duration in excess of predetermined criterion. A signal processor including a P-wave duration timer determines durations of detected P-waves. The selected characteristic of the sensed atrial activity indicative of an interatrial conduction disturbance may further be an average P-wave duration in excess of a predetermined criterion wherein the signal processor includes a duration averager coupled to the P-wave duration timer that averages determined P-wave durations.

In accordance with further aspects of the present invention, the selected characteristic of the sensed atrial activity indicative of an interatrial conduction disturbance is an interatrial delay time exceeding a predetermined criterion, wherein a first detector detects right atrial activations and a second detector detects left atrial activations. The signal processor includes an interatrial delay timer coupled to the first and second detectors that determines if interatrial delay times between activations detected by the first detector and the second detector exceed the predetermined criterion.

In accordance with further aspects of the present invention, the atrial arrhythmia prevention pacing pulses are atrial overdrive pacing pulses and the pulse generator circuit includes an atrial overdrive pulse generator that provides atrial overdrive pacing pulses to the heart when the interatrial conduction disturbance is detected.

In accordance with a further aspect of the present invention, a detector detects P-waves of the heart and the pulse generator circuit includes an atrial pulse generator that delivers an atrial pacing pulse a delay time after each detected P-wave. The implantable medical device may further include a P-wave duration timer coupled to the detector that determines durations of detected P-waves and a pacing control that varies the delay time responsive to determined P-wave durations.

In accordance with a further aspect of the present invention, the implantable medical device may include a P-wave alternans analyzer that analyzes a selected characteristic of detected odd and even P-waves and wherein the discriminator determines if the difference between the selected characteristic of odd and even P-waves exceeds a predetermined criterion indicative of an interatrial conduction disturbance.

In accordance with a further aspect of the present invention, the interatrial conduction disturbance is a predetermined or predetermined change in spectral energy distribution of the sensed P-waves. To that end, the implantable medical device includes a spectral analyzer that performs spectral energy distribution analysis of the sensed P-waves.

The implantable medical device may further include a pacing control that causes the output circuit to cease the delivery of atrial arrhythmia prevention pacing pulses to the heart when the interatrial conduction disturbance is terminated evidenced by the satisfaction of a second predetermined criterion in the sensed atrial activity.

The present invention still further provides a method of pacing the heart to prevent pathologic atrial tachyarrhythmia, as illustrated above, of the heart. The method includes the steps of sensing atrial activity of the heart, detecting an interatrial conduction disturbance, and delivering atrial arrhythmia prevention pacing pulses to the heart in response to the detection of the interatrial conduction disturbance.

BRIEF DESCRIPTION OF THE DRAWINGS

The features of the present invention which are believed to be novel are set forth with particularity in the appended claims. The invention, together with further objects and advantages thereof may best be understood by making reference to the following description taken in conjunction with the accompanying drawings, in the several figures of which like reference characters identify identical elements, and wherein:

DETAILED DESCRIPTION OF THE PREFERRED EMBODIMENTS

While the preferred embodiment is directed toward atrial fibrillation prevention pacing, this is for illustration purposes and it is within the scope of the present invention to provide detection of any interatrial conduction disturbance and thereafter to provide any type of atrial arrhythmia preventative pacing pulses.

Figure 1:
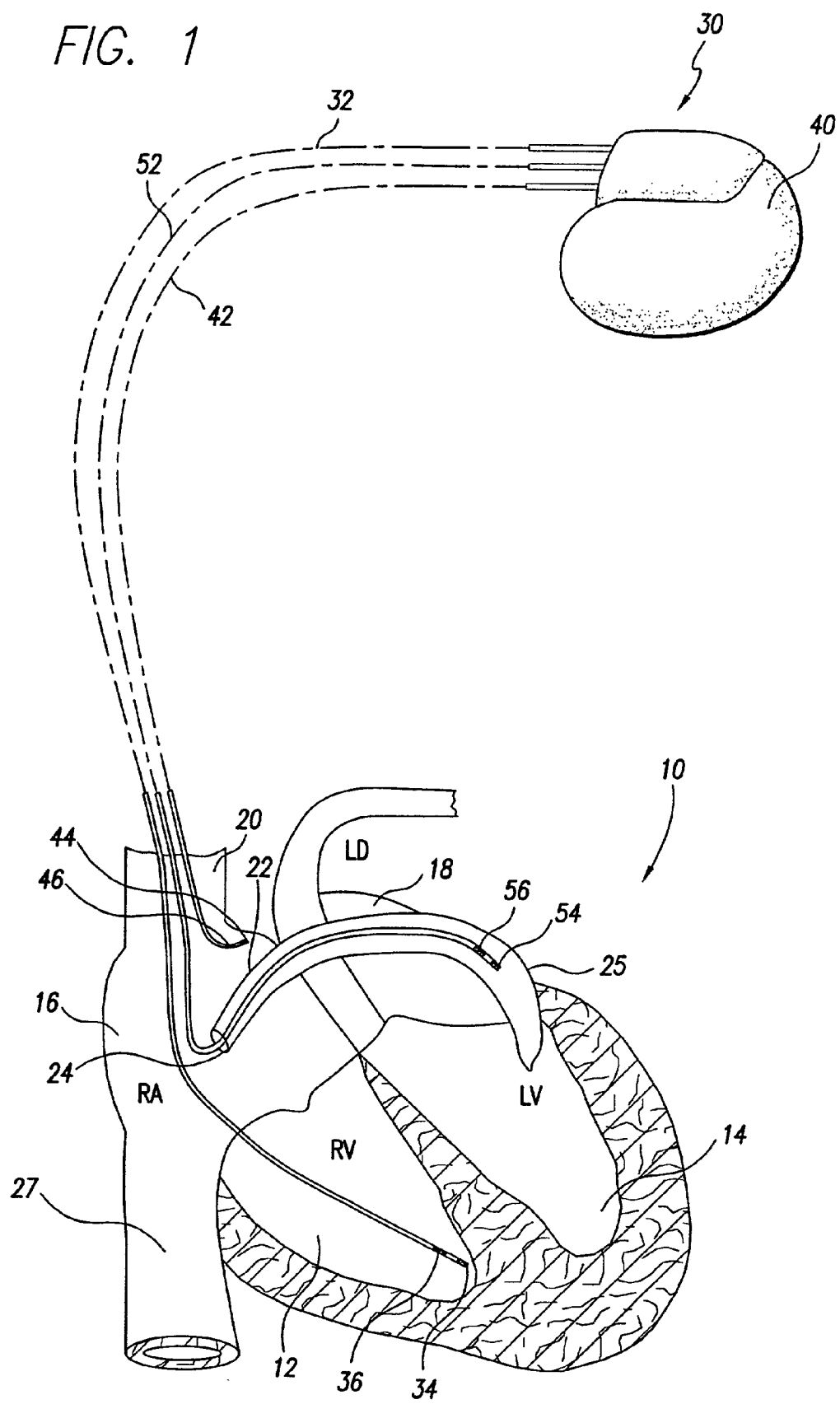
FIG. 1 is a schematic illustration of a human heart in need of cardiac rhythm management and atrial fibrillation prevention pacing shown in association with an implantable medical device embodying the present invention.

Referring now to FIG. 1, it illustrates a heart 10 in need of cardiac rhythm management and atrial fibrillation prevention pacing shown in association with an implantable medical device 30 embodying the present invention. The portions of the heart 10 illustrated in FIG. 1 are the right ventricle 12, the left ventricle 14, the right atrium 16, and the left atrium 18. Also illustrated are the superior vena cava 20, the coronary sinus 22, the os or opening to the coronary sinus 24, and the great cardiac vein 25. As is well known in the art, the implantable medical device 30 is arranged to be implanted in an upper left chest portion of a patient within a subcutaneous pocket.

The implantable medical device 30 includes a first endocardial lead 32 having an electrode pair including a distal electrode 34 and a proximal electrode 36. The electrodes 34 and 36 are disposed or implanted in the right ventricle 12 to permit the sensing of ventricular activity and the application of pacing pulses to the right ventricle. The implantable medical device 30 further includes a second endocardial lead 42 having an electrode pair including a distal electrode 44 and a proximal electrode 46. The electrodes 44 and 46 are disposed or implanted in the right atrium 16 of the heart 10 to permit sensing of right atrial activity and the application of pacing pulses to the right atrium. The implantable medical device 30 still further includes an intravascular lead 52 having an electrode pair including a distal electrode 54 and a proximal electrode 56. The electrodes 54 and 56 are disposed or implanted in the coronary sinus vein 25 of the heart 10 adjacent the left atrium 18. The electrodes 54 and 56 permit sensing of left atrial activity and the application of pacing pulses to the left atrium 18. As will be seen hereinafter, one of electrodes 54 and 56 may be utilized with one of electrodes 44 and 46 for broad field sensing of atrial activity to eliminate restrictions of a very narrow view of electrical activity of the atria.

As will also be seen hereinafter, electrodes 44 and 46 may be placed in parallel and used for sensing atrial activity (with the conductive enclosure 40 of the implantable medical device 30 as the reference) to provide an alternate approach for broad field sensing of atrial activity of the heart 10.

Figure 2:
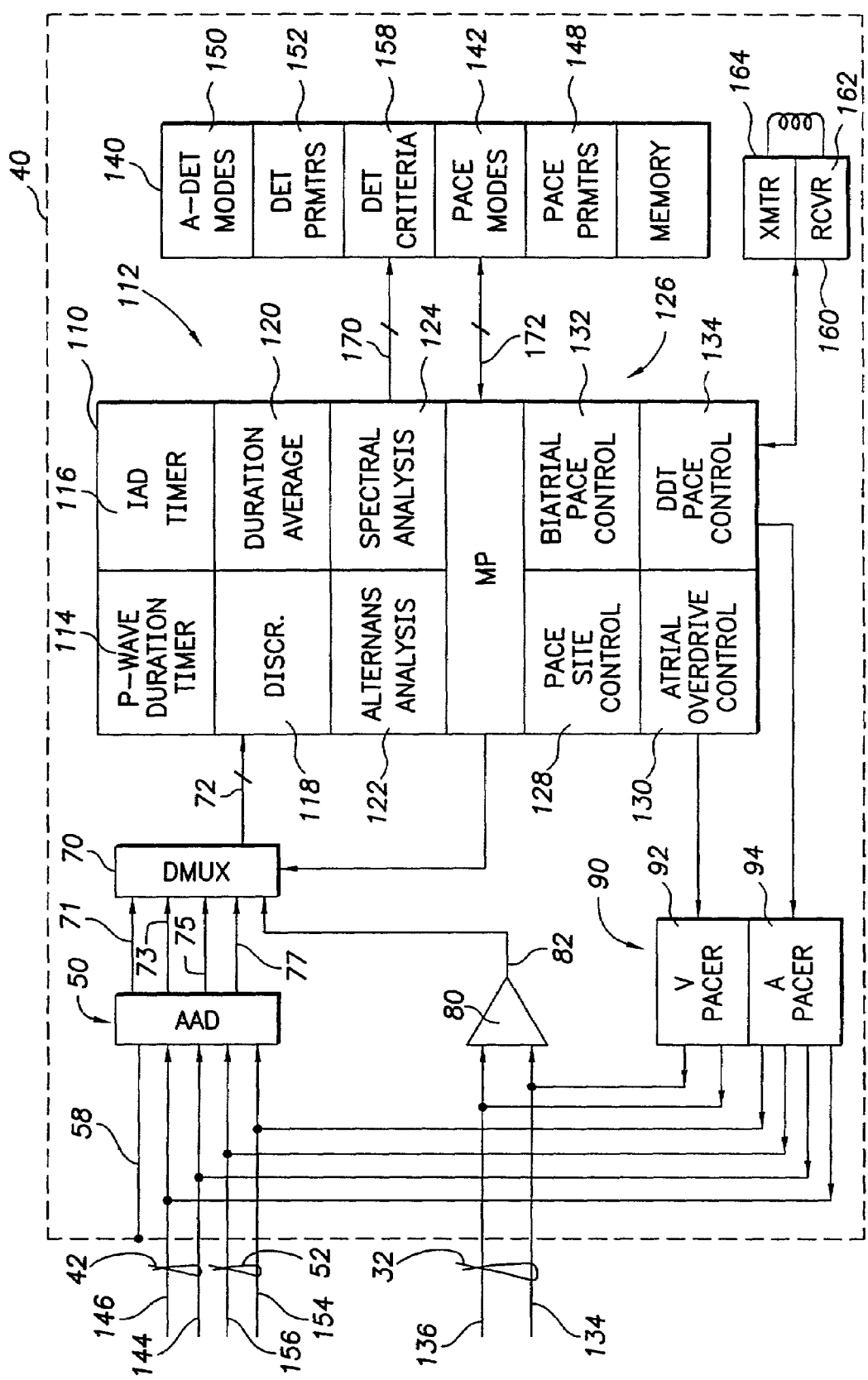
FIG. 2 is a block diagram of the implantable medical device of FIG. 1.

As illustrated in FIG. 2, the implantable medical device 30 includes within the enclosure 40 an atrial activity sensing system 50, a digitizing multiplexer 70, a ventricular sense amplifier 80, a pulse generator circuit 90, and a microprocessor 110. The implantable medical device 30 further includes a memory 140 and a telemetry circuit 160.

Figure 3:
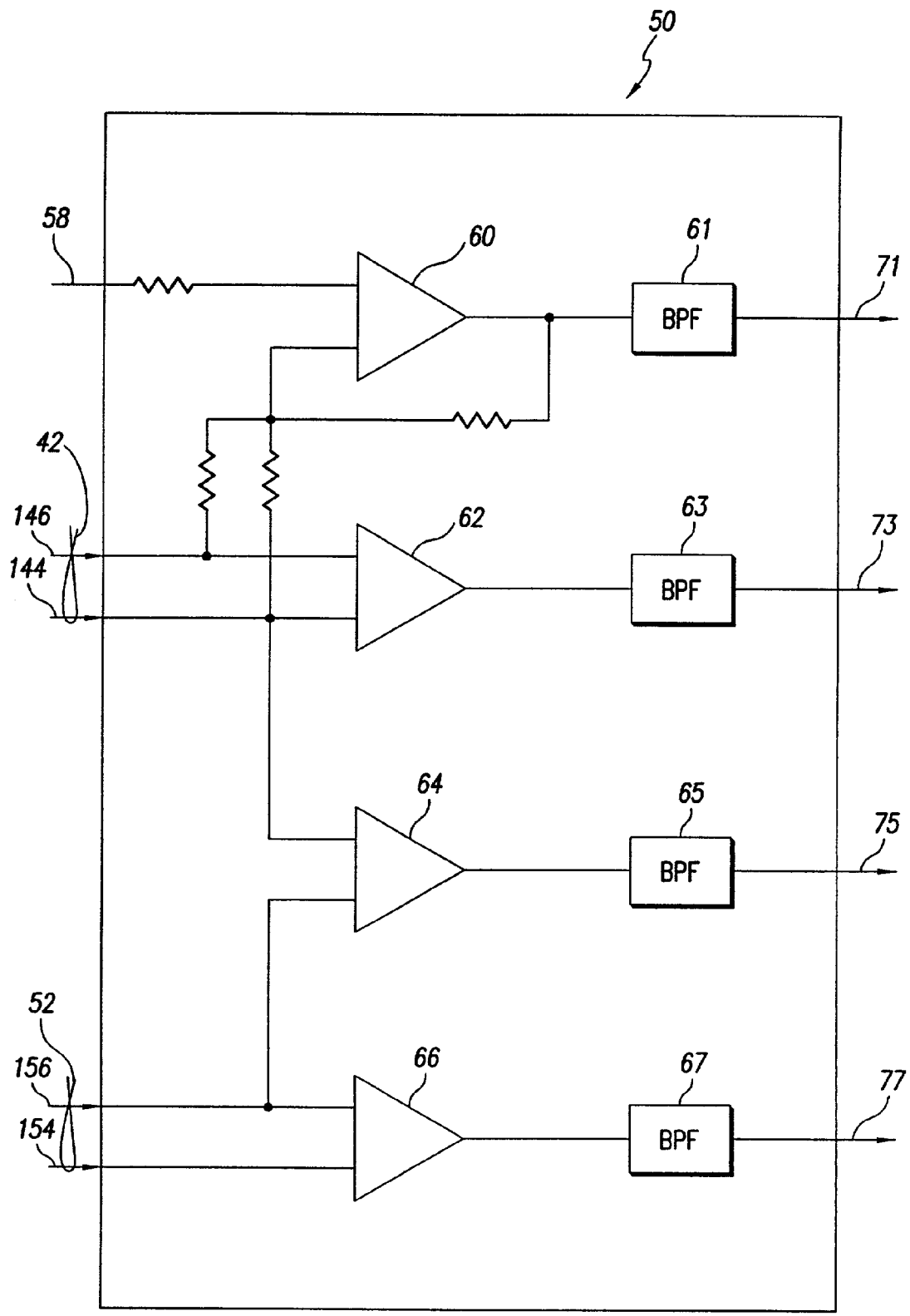
FIG. 3 is a block diagram of the atrial activity detector of the implantable medical device of FIG. 2.

The atrial activity sensing system 50 detects atrial activity of the heart 10. To that end, and as may be seen in greater particularity in FIG. 3, the atrial activity sensing system 50 includes sense amplifiers 60, 62, 64, and 66. Sense amplifier 60 has an input which is coupled to the conductive enclosure 40 of the implantable medical device 30 by a line 58. The other input of the sense amplifier 60 is resistively coupled to both electrodes 46 and 44 of lead 42 by conductors 146 and 144 respectively of lead 42. The output of sense amplifier 60 is coupled to a bandpass filter 61 having an output 71. The foregoing results in atrial activity being sensed between the parallel combination of electrodes 44 and 46 and the enclosure 40 of the implantable medical device 30. This provides broad field sensing of atrial activity of the heart 10.

Sense amplifier 62 has an input coupled to electrode 46 by the conductor 146 of lead 42 and another input coupled to electrode 44 of lead 42 the conductor 144 of lead 42. The output of sense amplifier 62 is coupled to a bandpass filter 63 having an output 73. The output 73 provides a signal representing atrial activity of the right atrium which is sensed in the right atrium in a differential mode. This provides a crisp identification of P-waves of the detected atrial activity by responding to the "local" higher frequency content of the signal.

Sense amplifier 66 has an input which is coupled to electrode 56 of lead 52 by a conductor 156 of lead 52 and another input coupled to electrode 54 by another conductor 154 of lead 52. The output of sense amplifier 66 is coupled to a bandpass filter 67 having an output 77 which provides a signal representing atrial activity of the left atrium. The atrial activity sensed by electrodes 54 and 56 is sensed locally and differentially to provide crisp indications of P-waves of the left atrium.

Lastly, sense amplifier 64 has an input which is coupled to electrode 44 of lead 42 by conductor 144 and another input coupled to the electrode 56 of lead 52 by conductor 156. The output of sense amplifier 64 is coupled to a bandpass filter 65 having an output 75 which provides a signal representing atrial activity sensed between electrode 56 of lead 52 and electrode 44 of lead 42. This provides an alternative approach to sensing of atrial activity.

Each of the outputs 71, 73, 75, and 77 of the atrial activity sensing system 50 is coupled to an input of the digitizing multiplexer 70. As will be seen hereinafter, under control of the microprocessor 110, the digitizing multiplexer selects selected ones of the atrial activity sensing system outputs for use in determining when atrial fibrillation prevention pacing is required.

Returning to FIG. 1, the ventricular sense amplifier 80 has an input which is coupled to electrode 36 of lead 32 by a conductor 136 of lead 32. It also includes another input which is coupled to electrode 34 of lead 32 by another conductor 134 of lead 32. While the ventricular sense amplifier 80 is shown configured to sense in a bipolar fashion between electrodes 34 and 36, this is for illustration purposes only and one of skill in the art could readily adapt the sense amplifier 80 to switch in the conductive enclosure 40 as a reference electrode to provide unipolar sensing. Accordingly, unipolar ventricular sensing is within the spirit of the invention. An output 82 provides a signal to the digitizing multiplexer 70 representing ventricular activity of the heart detected or sensed in the right ventricle.

The pulse generator 90 provides pacing pulses to the heart under control of the microprocessor 110. It thus provides pacing to the heart to provide regular pacing therapy and in addition, in accordance with the present invention, atrial fibrillation prevention pacing therapy as well. The pulse generator 90 includes a ventricular pulse generator 92 having outputs coupled to electrodes 36 and 34 of lead 32 by conductors 136 and 134 of lead 32. This enables the ventricular pulse generator 92 to apply pacing pulses to the right ventricle.

The pulse generator 90 further includes an atrial pulse generator 94 having a first pair of outputs coupled to electrodes 44 and 46 of lead 42 by the conductors 144 and 146 of lead 42. The atrial pulse generator 94 includes a second pair of outputs coupled to electrodes 56 and 54 of lead 52 by conductors 156 and 154 of lead 52. While the ventricular pulse generator 92 and the atrial pulse generator 94 are shown configured to generate pacing pulses in a bipolar fashion, this is for illustration purposes only and one of skill in the art could readily adapt the pulse generators 92 and 94 to selectively switch in the conductive enclosure 40 as a reference electrode in place of the electrodes 36, 46, and 56 to provide unipolar pacing pulses in a respective chamber of the heart. Accordingly, unipolar atrial, biatrial and ventricular stimulation are within the spirit of the invention. This enables the atrial pulse generator 94 to apply pacing pulses to either the right atrium or the left atrium or simultaneously to both atria. The atrial fibrillation prevention pacing modalities which may be employed in accordance with the preferred embodiments of the present invention will be described subsequently.

The microprocessor 110 controls the overall functioning of the implantable medical device 30. To implement such control, the microprocessor executes operating instructions stored in the memory 140 and utilizes various parameters also stored in memory 140. For example, the memory 140 stores, in a storage location 142, the operating instructions defining the various pacing modalities, including the atrial arrhythmia prevention modalities including atrial fibrillation prevention pacing modalities in accordance with the present invention, which may be provided by the implantable medical device 30. Pacing parameters may be stored in a storage location 148. Further, to support the detection of atrial activity requiring atrial fibrillation prevention pacing, operating instructions defining atrial detection modalities are stored in storage location 150, atrial detection parameters are stored in memory location 152 and detection criterion are stored in memory location 158.

The telemetry circuit 160 permits mode selections and parameter storage in the memory 140 to be made through the use of an external programmer (not shown) of the type well known in the art. The telemetry circuit includes a receiver 162 which receives telemetry commands including mode and parameter selections from the programmer. The receiver 162 conveys the commands to the microprocessor 110 which then stores them in the memory 140. The telemetry circuit 160 also includes a transmitter 164. The transmitter may be used for transmitting data to the programmer. The transmitted data may include sensed electrograms or status information, for example, as is well known in the art.

The microprocessor 110 is coupled to the memory 140 by a multiple-bit address bus 170 and a bi-directional, multiple-bit data bus 172. The microprocessor 140 uses the address bus 170 to fetch operating instructions or parameters from the memory at address locations defined on the address bus 170. The fetched instructions and parameters are conveyed to the microprocessor 140 over the data bus 172. Similarly, the microprocessor 110 may store data in the memory 140 at memory locations defined on the address bus 170. The microprocessor 110 conveys the data to the memory over the data bus 172. Such microprocessor and memory operation are conventional in the art.

When executing the operating instructions stored in the memory 140, the microprocessor 110 implements a number of functional stages in accordance with the present invention. The functional stages are divided into a first group 112 for determining when detected atrial activity satisfies a predetermined criterion to require atrial fibrillation prevention pacing, and a second group 126 which controls the provision of the atrial fibrillation prevention pacing.

The first group of functional stages includes a P-wave duration timer 114, an interatrial delay timer 116, a discriminator stage 118, a P-wave duration averaging stage 120, an alternans analysis stage 122, and a spectral analysis stage 124. The second group of stages 126 includes a pace site control stage 128, an atrial overdrive control stage 130, a biatrial pace control stage 132, and a DDT pace control stage 134.

In accordance with a first aspect of the present invention, the implantable medical device 30 determines that the heart 10 is in need of atrial fibrillation prevention pacing based upon P-wave duration. More particularly, if a P-wave of a cardiac cycle is longer than, for example, 140 milliseconds, indicative of an interatrial conduction disturbance, the discriminator stage 118 will cause the heart to be paced in one of the atrial fibrillation prevention pacing modalities to be described hereinafter. In accordance with this aspect of the present invention, the microprocessor, during regular pacing by the implantable medical device 30 required for the patient and programmed by the physician, measures the duration of the P-waves occurring during each cardiac cycle. To this end, the microprocessor, from an output 72 of the digitizing multiplexer, monitors the digitized electrograms resulting from the electrogram provided by the atrial activity sensing system 50 at its output 73. The electrogram thus monitored for this purpose is the electrogram resulting from the sensing of atrial activity in the right atrium by the electrode pair 44 and 46.

The P-wave duration timer 114 detects each P-wave by monitoring zero crossings of the atrial electrogram and measures the time period between zero crossings of each P-wave. If a P-wave duration satisfies a predetermined condition by, for example, being longer than 140 milliseconds, it will cause the second group 126 of functional stages to provide atrial prevention pacing in accordance with a selected atrial prevention pacing modality.

In accordance with a further aspect of the present invention, the selected characteristic of the detected atrial activity for determining the presence of interatrial conduction disturbance and the need of atrial fibrillation prevention pacing, may be averaged P-wave duration. To this end, the microprocessor 112 may cause the digitizing multiplexer 70 to digitize the electrograms occurring at outputs 71 and 73 of the atrial activity sensing system 50. The digitized electrogram of output 71 would in this case be a broad field sensed electrogram sensed between the parallel combination of electrodes 44 and 46 and the conductive enclosure 40 of the implantable medical device 30. The broad field electrograms may be stored in the memory 140 and the electrogram derived from output 73 may be utilized to line up the detected P-waves to permit the duration average stage 120 to conduct a point-by-point average. Once a predetermined number of P-wave durations have been averaged, for example, 100 P-waves, the discriminator 118 will then determine if the averaged P-wave duration satisfies a predetermined criterion. For example, the predetermined criterion may be an averaged P-wave duration greater than 140 milliseconds. If the averaged P-wave duration is greater than the predetermined criterion, the discriminator stage 118 will then cause the second group of functional stages 126 to provide the heart with atrial fibrillation prevention pacing pulses in accordance with a selected atrial fibrillation prevention pacing modality.

In accordance with this further aspect of the present invention, the far-field P-waves to be averaged may be derived from output 75 of the atrial activity sensing system 50. This atrial activity electrogram results from the sensing of atrial activity between electrode 56 in the great cardiac vein and electrode 44 in the right atrium. This will also provide a far-field atrial electrogram for providing the P-waves to be averaged by the duration average stage 120. Here again, the atrial electrogram from output 73 may be utilized to line up the P-waves to be averaged for data analysis.

Also in accordance with this embodiment, the bandpass filter 65 may be chosen to have a broad bandpass for detecting low frequency components of the atrial activity. When combined with a signal averaging technique based on, for example, 100 or 1000 cardiac cycles, ambient noise that would be otherwise detected may be eliminated.

In accordance with a further aspect of the present invention the selected characteristic of the detected atrial activity for detecting an interatrial conduction disturbance and the need for atrial fibrillation prevention pacing may be based upon P-wave alternans analysis. Here, for example, a predetermined characteristic of the odd and even P-waves may be averaged by the alternans analysis stage 122. If the average predetermined characteristic of the odd and even P-waves when compared by discriminating stage 118 satisfies a predetermined criterion, the discriminating stage 118 will cause the second group of functional stages 126 to provide the atrial fibrillation prevention pacing.

In accordance with this embodiment, the alternans characteristic to be monitored may be, for example, P-wave height, P-wave duration, or the area under the P-wave electrogram. If the averaged characteristic of the odd and even P-waves differ by, for example, more than two percent (2%), this will satisfy the predetermined criterion and thus cause the provision of the atrial fibrillation prevention pacing. The atrial electrograms which may be used for the alternans analysis may be derived from either output 73 of the atrial activity sensing system 50 or the output 77 of the atrial activity sensing system. Either output, by providing an electrogram detected locally within a selected one of the atria, will provide a suitable signal for the alternans analysis.

In accordance with a still further aspect of the present invention, the selected characteristic of the detected atrial activity for detecting an interatrial conduction disturbance and the need for atrial fibrillation prevention pacing may be interatrial delay. Here, the microprocessor preferably monitors the digitized electrograms derived from outputs 73 and 77 of the atrial activity sensing system 50. The interatrial delay timer 116 will detect when a P-wave occurs in the right atrium and the left atrium and measures the time between the beginning of P-waves in those two chambers. The time between the beginning of the same P-wave within the right atrium and the left atrium is the interatrial delay. If the discriminating stage 118 determines that the interatrial delay of a cardiac cycle is greater than the predetermined criterion of, for example, 50 milliseconds, it will cause the second group of functional stages 126 to provide the atrial fibrillation prevention pacing. Alternatively, if the discriminating state 118 detects a change in the interatrial delay which exceeds a predetermined limit, for example 25 ms, it will cause the second group of functional stages to provide atrial fibrillation prevention pacing.

Lastly, in accordance with a still further-aspect of the present invention, the selected characteristic of the detected atrial activity for detecting an interatrial conduction disturbance and the need for atrial fibrillation prevention pacing may be spectral analysis of the P-waves. Here, the spectral analysis stage 124 will monitor the digitized atrial electrograms derived from output 73, for example, of the atrial activity sensing system 50. It performs a spectral analysis of each P-wave. After spectral analysis, the discriminating stage 118 will analyze the spectrum analysis to determine if there has been a shift in the spectral energy distribution of each P-wave. If the discriminator 118 determines that there has been a shift to more energy in the higher frequency bands of a P-wave, it will then cause the second group of functional stages 126 to provide the atrial fibrillation prevention pacing.

Any one of the foregoing methods and structures may be used for detecting an interatrial conduction disturbance and the need for atrial fibrillation prevention pacing. In accordance with of the present invention, the atrial fibrillation prevention pacing may be atrial overdrive pacing or DDT pacing.

In the case of atrial overdrive pacing, the atrial overdrive control stage 130 causes the atrial pulse generator 94 to deliver pacing pulses to one or both of the atria at a rate which is faster than then intrinsic atrial rate of the heart. To that end, the atrial pulse generator may apply the overdrive atrial pacing pulses to the right atrial lead 42, to left atrial lead 52, or to both leads simultaneously in either a unipolar or a bipolar fashion.

In one embodiment, a conventional DDT mode of pacing may be employed to control the interatrial conduction disturbance. For example, by sensing in the right atrium and directing the triggered pacing pulse to stimulate the left atrium, the device would effectively overdrive the left atrium and reduce the interatrial conduction disturbance.

In a second embodiment, a modified DDT mode of pacing may be employed to control the interatrial conduction disturbance, wherein the time between the sensing of P-wave in the right atrium and the stimulation pluses (A-pulse) in the left atrium is programmable, i.e., a programmable P-A delay. In accordance with a further aspect of this embodiment, the duration of the P-wave may be a criterion for selecting the P-A delay, either by the clinician or automatically by the implantable medical device. More specifically, the P-A delay may be varied inversely with the P-wave duration. Accordingly, this modification of the DDT mode could provide greater control for reducing the interatrial conduction disturbances.

In accordance with a still further aspect of the present invention, the atrium to be paced may be adjusted by the biatrial pace control 132 based upon the chamber in which the P-waves are initially detected. For example, if the P-waves are initially detected in the right atrium, the left atrium may be paced. If the P-waves are initially detected in the left atrium, the right atrium may be paced.

During delivery of the atrial fibrillation prevention pacing pulses, the selected characteristic of the atrial activity used to determine the need for the atrial fibrillation prevention pacing therapy may be monitored. If the selected characteristic of the detected atrial activity satisfies a second predetermined criterion, the discriminating stage 118 will then terminate the atrial fibrillation prevention pacing therapy and return the device to its regular pacing modality since the interatrial conduction disturbance will have subsided or will have been terminated. For example, if the need for atrial fibrillation prevention pacing is based upon P-wave duration, the atrial fibrillation prevention pacing may allow periodic pauses in the pacing rate to permit measurement of intrinsic P-waves to determined if the atrial fibrillation prevention pacing should be terminated, using as a criterion of, for example, a P-wave duration below 130 ms. Of course, the second predetermined criterion may be the same as the first predetermined criterion for determining the need for atrial fibrillation prevention pacing, or it could be a different criterion as in the example above.

While particular embodiments of the present invention have been shown and described, modifications may be made, and it is therefore intended in the appended claims to cover all such changes and modifications which fall within the true spirit and scope of the invention.

What is claimed is:

1. A method of pacing a heart to prevent an atrial arrhythmia, the method comprising the steps of:
   detecting an interatrial conduction disturbance of the heart; and
   delivering atrial arrhythmia prevention pacing pulses to the heart responsive to detecting the interatrial conduction disturbance;
   wherein the interatrial conduction disturbance is a P-wave duration in excess of a predetermined criterion and wherein the method further comprises the step of determining durations of detected P-waves.

2. The method of claim 1, wherein the interatrial conduction disturbance is an average P-wave duration in excess of a predetermined criterion and wherein the method further comprises the step of averaging the determined P-wave durations.

3. The method of claim 1, wherein the interatrial conduction disturbance is an interatrial delay time in excess of a predetermined criterion and wherein the method further comprises the steps of detecting right atrial activations, detecting left atrial activations, and timing interatrial delay times between right atrial activation detection and left atrial activation detection.

4. The method of claim 1, wherein the atrial arrhythmia prevention pacing pulses are atrial overdrive pacing pulses and wherein the delivering step comprises providing atrial overdrive pacing pulses to the heart.

5. The method of claim 1, wherein the delivery step includes delivering right atrial pacing pulses and left atrial pacing pulses.

6. The method of claim 1, further including the step of terminating the delivery of the atrial fibrillation prevention pacing pulses to the heart when the interatrial conduction disturbance ceases.

7. A method of pacing a heart to prevent an atrial arrhythmia, the method comprising the steps of:
   detecting an interatrial conduction disturbance of the heart;
   delivering atrial arrhythmia prevention pacing pulses to the heart responsive to detecting the interatrial conduction disturbance;
   detecting P-waves of the heart and wherein the delivering step comprises delivering an atrial pacing pulse at a delay time after each detected P-wave; and
   determining durations of detected P-waves and wherein the delivering step further comprises varying the delay time responsive to determined P-wave durations.

8. The method of claim 7, wherein the delivering step further comprises varying the delay time in an inverse relation to determined P-wave durations.

9. A method of pacing a heart to prevent an atrial arrhythmia, the method comprising the steps of:
   detecting an interatrial conduction disturbance of the heart;
   delivering atrial arrhythmia prevention pacing pulses to the heart responsive to detecting the interatrial conduction disturbance; and
   detecting P-waves of the heart, wherein the interatrial conduction disturbance is a selected difference between detected odd and even P-waves exceeding a predetermined criterion, and wherein the detecting step comprises determining if the selected difference between the odd and even P-waves exceeds a predetermined criterion.

10. A method of pacing a heart to prevent an atrial arrhythmia, the method comprising the steps of:
    detecting an interatrial conduction disturbance of the heart;
    delivering atrial arrhythmia prevention pacing pulses to the heart responsive to detecting the interatrial conduction disturbance; and
    detecting P-waves of the heart, wherein the interatrial conduction disturbance is a predetermined spectral energy distribution of detected P-waves, and wherein the method further comprises the step of performing spectral energy distribution analysis of the detected P-waves.

11. A method of pacing a heart to prevent an atrial arrhythmia, the method comprising the steps of:
   detecting an interatrial conduction disturbance of the heart; and
   delivering atrial arrhythmia prevention pacing pulses to the heart responsive to detecting the interatrial conduction disturbance;
   wherein detecting the interatrial conduction disturbance of the heart comprises sensing broad near-field atrial activity.

12. A method of pacing a heart to prevent an atrial arrhythmia, the method comprising the steps of:
   detecting an interatrial conduction disturbance of the heart; and
   delivering atrial arrhythmia prevention pacing pulses to the heart responsive to detecting the interatrial conduction disturbance;
   wherein detecting the interatrial conduction disturbance of the heart comprises sensing near-field atrial activity and far-field atrial activity.

* * * * *